United States Patent [19]

Carson et al.

[11] Patent Number: 5,416,075

[45] Date of Patent: May 16, 1995

[54] BIOSPECIFIC EMULSIONS

[75] Inventors: Robert G. Carson, Rahway, N.J.; Kurt M. Schilling, Parkgate, England; Bijan Harichian, South Orange, N.J.; Van Au, Congers, N.Y.

[73] Assignee: Chesebrough-Pond's USA Co., Division of Conopco, Inc., Greenwich, Conn.

[21] Appl. No.: 159,994

[22] Filed: Nov. 30, 1993

[51] Int. Cl.$^6$ .......................... A61K 7/06; A61K 7/48; A61K 31/71

[52] U.S. Cl. ............................... 514/23; 514/2; 514/8; 514/15; 514/844; 514/859; 514/860; 514/873; 514/880; 514/881; 514/901; 514/938; 514/975; 252/302; 252/304; 252/306; 252/312; 252/DIG. 5; 252/DIG. 13; 424/49; 424/58; 424/59; 424/61; 424/70.1; 424/196.1; 424/70.14

[58] Field of Search ................ 514/2, 8, 15, 23, 844, 514/859, 860, 873, 880, 881, 901, 938, 975; 252/302, 304, 306, 312, DIG. 5, DIG. 13; 424/49, 58, 59, 61, 70, 196.1

[56] References Cited

U.S. PATENT DOCUMENTS

| | | | |
|---|---|---|---|
| 4,413,073 | 11/1983 | Gibson et al. | 523/511 |
| 4,600,526 | 7/1986 | Gallot et al. | 514/938 |
| 4,605,422 | 8/1986 | Goddard et al. | 44/51 |
| 4,818,817 | 4/1989 | Shoham et al. | 536/1.11 |
| 4,870,010 | 9/1989 | Hayes | 424/70 |
| 4,911,736 | 3/1990 | Huang et al. | 44/51 |
| 4,943,390 | 7/1990 | Hayes et al. | 252/DIG. 6 |
| 4,971,788 | 11/1990 | Tabibi et al. | 424/49 |
| 4,992,420 | 2/1991 | Neeser | 514/8 |
| 4,994,441 | 2/1991 | Neeser | 424/48 |
| 4,999,195 | 3/1991 | Hayes | 424/70 |
| 5,002,759 | 3/1991 | Gaffar et al. | 424/49 |
| 5,011,678 | 4/1991 | Wang et al. | 514/975 |
| 5,023,271 | 6/1991 | Vigne et al. | 514/788 |
| 5,043,155 | 8/1991 | Puchalski et al. | 424/78 |
| 5,071,977 | 12/1991 | Cassels et al. | 536/123 |
| 5,130,122 | 7/1992 | Tabibi et al. | 424/49 |
| 5,190,747 | 3/1993 | Sekiguchi et al. | 514/975 |
| 5,234,909 | 8/1993 | Philippe | 514/975 |

OTHER PUBLICATIONS

Chemical Abstracts 115:286 971g (Abstract of JP 03/220130).
Goldberg, Sarit et al. "Bacterial Desorption by Commercial Mouthwashes vs. Two-Phase Oil:Water Formulations" Biofouling, (1991), vol. 3, pp. 193–198.
U.S. Patent Abstract 7 349 772.

*Primary Examiner*—Ronald W. Griffin
*Attorney, Agent, or Firm*—Rimma Mitelman

[57] ABSTRACT

Oil-in-water emulsions can be formed using surfactants with biospecific headgroups. Emulsion droplets adhere to surfaces of microorganisms or to various biological surface bearing appropriate adhesins, thus delivering surfactant materials directly to various surfaces. Lipophilic materials and essential oils can be targeted in this way. The emulsions may be incorporated into oral hygiene non-food compositions or compositions for topical application to skin, hair or nails.

18 Claims, No Drawings

BIOSPECIFIC EMULSIONS

FIELD OF THE INVENTION

The invention relates to oil-in-water emulsions containing an amphipathic compound which carries at the head end of its hydrophilic part a moiety recognized by adhesins on microorganisms or on a biological surface. The invention also relates to use of the emulsions to deliver amphipathic compounds alone, or in combination with lipohilic active agents, to the surfaces of microorganisms or to various biological surfaces.

BACKGROUND OF THE INVENTION

Indigenous bacteria and other microorganisms (e.g., yeasts) present in an oral cavity or on other biological surfaces adhere to various substrates (e.g., microorganisms of the same or different genus, teeth surface, epithelial surface) via receptor-modulated recognition mechanisms. Microorganisms in general express structures, generally termed "adhesins" which recognize and bind selectively to specific moieties called "receptors" found on microorganisms' surface or biological surfaces (e.g., teeth, oral cavity, skin, hair, or nails.) For example, some microorganisms express proteinaceous structures called "lectins" which recognize specific carbohydrate moieties; other microorganisms recognize specific peptide fragments of proteins (e.g., fibronectin) which typically form part of an epithelial surface. The adhesin/receptor modulated recognition mechanisms allow microorganisms to adhere with a high degree of selectivity and specificity to other microorganisms (of the same or different genus and/or species) and/or to a biological surface.

Recognition mechanisms of many microorganisms present in an oral cavity and on other biological surfaces have been identified. Fucose specific lectins have been described for several oral bacterial species, including those belonging to the genera Actinomyces, Capnocytophaga, and Streptococcus. Rhamnose specific lectins have been isolated from oral species including Capnocytophaga species. By far, the lectins most commonly expressed by plaque bacteria are $\beta$-galactoside specific or "lacto sensitive" adhesins. The genera of the oral bacteria which produce $\beta$-galactoside specific adhesins cover a diverse taxonomic range including Actinomyces, Streptococcus, Porphyromonas, Fusobacterium, Haemophilus, Capnocytophaga, Veillonella, Prevotella, Staphilococcus and Neisseria; these represent both primary and secondary colonizers of the teeth.

Numerous skin microorganisms interact with epithelial substrates through receptor-modulated recognition between cells' surfaces. Various skin microorganisms adhere preferentially to specific sites on various body surfaces. For example, Staphylococcus aureus, Streptococcus pyogenes and Pseudomonas aeruginosa adhere to collected nasal epithelial cells. Corynebacterium minutissimum and C. xerosis bind to epidermal cells. Yeast species such as Candida albicans, C. stellatoidea, C. parapsilosis, C. tropicales, C. krusei and C. guilliermondii bind to corneocytes. Dermatophytes such as Trichophyton quinckeanum, T. interdigitale and T. rubrum bind to keratinocytes from the sole of the foot, palm, dorsum of the hand, forearm and knee. Although the recognition process is complex, some of the specific structures involved in adherence of skin microorganisms are known. Polymeric glucosamine (chitosan) can inhibit the adherence of C. albicans to corneocytes. Lipoteichoic acid is the adhesin which Streptococcus pyogenes uses to attach itself to oral mucosal cells and this acid is also involved in the attachment of various streptococcal species to human stratum corneum cells. Lipoteichoic acid also interacts with the host cell receptors, one of which is fibronectin. Fibronectin carries two separate binding sites, one for streptococci and one for staphylococcii. Glucose and mannose washes have been used to remove coryneform and streptococcal species from the skin. Common skin microbes such as coryneform species involved in malodor generation and opportunistic pathogenic streptococcal species carry structures that recognize carbohydrates as well as fibronectin. Epithelial cells have "adhesin" recognition structures which interact with fatty acid side chains of lipoteichoic acid.

The use of specific structures such as saccharides, oligosaccharides, polysaccharides and glycoproteins to inhibit bacterial adherence and reduce associated accumulation of microbial films is dislosed in a number of patents: U.S. Pat. No. 4,349,772 details the use of an oligosaccharide derived from S. sanguis to prevent oral plaque accumulation; U.S. Pat. No. 5,002,759 describes use of an oligosaccharide to prevent adherence of Streptococcus pyogenes to epithelial cells; U.S. Pat. Nos. 4,992,420 and 4,994,441 disclose the use of milk-derived glycoproteins, e.g., $\kappa$-casein, to prevent plaque accumulation. Japanese patent application 03220130 discloses the use of $\kappa$-casein in dentrifices.

U.S. Pat. Nos. 5,130,122 and 4,971,788 describe dental hygiene products containing oil-in-water emulsions. A paper by S. Goldberg and M. Rosenberg, "Bacterial Desorption by Commercial Mouthwash vs. Two-Phase Oil:Water Formulations" (Biofouling, 3, 193–198, 1991) discusses the use of emulsions to remove in vitro bacterial films.

None of the above-cited publications describes an oil-in-water emulsion wherein oil droplets carry amphipathic molecules with biospecific head groups.

Although highly specific, the adhesin/receptor recognition interactions are non-covalent and generally reversible. Coaggregation reactions between complementary pairs of microrganisms or between microorganisms and biological surfaces can be inhibited by the presence in solution of the various moieties which are recognized by lectins. Competition for binding sites prevents or minimizes coaggregation or adherence. However, interactions between receptors and lectins are generally of low affinity. In nature, simultaneous, polyvalent (multisite) interactions between numerous adhesin/receptor pairs are used to achieve secure adherence.

It is an object of the present invention to provide a structure with multiple binding sites for binding to a microrganism or to a biological surface.

It is another object of the invention to provide an oil-in-water emulsion containing oil droplets carrying amphipathic molecules wherein the hydrophilic part of the amphipathic molecule contains a moiety recognized by a microorganism and/or by a biological surface.

It is yet another object of the invention to provide a composition for an effective delivery of an amphipathic compound to a microorganism or to a biological surface.

It is still another object of the invention to provide a method of delivering an amphipathic agent to a microorganism or to a biological surface.

It is still another object of the invention to provide an oil-in-water emulsion wherein oil droplets in the emulsion contain an active lipohilic ingredient and wherein oil droplets carry a biospecific amphipathic compound.

It is yet another object of the invention to provide a method of delivering an active lipophilic ingredient to the microorganism and/or to a biological surface.

It is yet another object of the invention to provide a composition for topical application to mammalian skin, hair, or nails which composition contains an oil-in-water emulsion including a biospecific amphipathic compound.

It is yet another object of the invention to provide an oral non-hygiene composition containing an oil-in-water emulsion which includes a biospecific amphipathic compound.

These and other objects of the invention will become more apparent from the detailed description and the examples that follow.

SUMMARY OF THE INVENTION

The above objects are accomplished by the present invention which includes an oil-in-water emulsion suitable for application to the surface of a microorganism and/or to a biological surface, the emulsion containing an aqueous phase, an oil phase, and an emulsifier system wherein the emulsifier system includes at least one amphipathic compound, wherein the amphipathic compound includes a biospecific moiety at the head end of its hydrophilic part.

The term "Biological surface" as used herein means mammalian teeth, oral epithelial surfaces, oral plaque, skin, hair, or nails. The term "skin" as used herein means the top layer of skin (i.e., stratum corneum) and other cellular surfaces in skin such as corneocytes and keratinocytes.

The term "Amphipathic" as used herein means a molecule or a compound having both hydrophilic and hydrophobic groups.

The term "Biospecific" as used herein means "containing a receptor," i.e., containing a moiety recognized by lectins or other adhesins (e.g., moieties which recognize protein, lipid or glycolipid structures) on microorganisms and/or on a biological surface.

The biospecific amphipathic compound in the emulsions according to the present invention has at least two functions: it acts as an emulsifier and, by virtue of possessing a biospecific moiety, it also targets to microorganisms and/or to a biological surface. The hydrophobic group of the amphipathic compound extends into an oil droplet, and the hydrophilic group protrudes into an aqueous phase. Oil droplets in the emulsion acording to the invention serve as substrates for a biospecific amphipathic compound; each oil droplet carries multiple molecules of an amphipathic compound. As a result, each oil droplet in the inventive emulsions provides a polyvalent binding site for a microorganism or another cell on a biological surface, since numerous adhesin/-receptor pairs are available to achieve adherence between a microorganism or a biological surface and a biospecific amphipathic compound.

Some amphipathic agents may have independent useful functions, in addition to being emulsifiers and targeting agents. For example, the longer chain N-alkyl aldobionamides are biospecific amphipathic compounds and are also antimicrobial agents.

In a preferred embodiment of the invention, oil droplets in the inventive emulsion contain a lipophilic active ingredient (e.g., a skin conditioning agent, an antimicrobial, a flavorant, a perfume, a UV-absorbing agent, a vitamin), which active can be delivered to the desired biological surface and/or to microorganisms effectively and with high specificity by virtue of an association of oil droplets with biospecific amphipathic agents. According to the present invention in order to associate an oil droplet with a biospecific compound, an oil-in-water emulsion is prepared with a biospecific compound which is amphipathic and thus serves as an emulsifier. Thus, oil droplets which carry multiple biospecific head groups are attained.

According to the present invention, the inventive emulsions may be incorporated into oral hygiene non-food compositions or into compositions for topical application to mammalian skin, hair, or nails. The present invention also includes methods of delivering a biospecific amphipathic compound, alone or in combination with an active lipophilic ingredient, to the surfaces of microorganisms or to various biological surfaces.

DETAILED DESCRIPTION OF THE EMBODIMENTS

Amphipathic Biospecific Compound

The amphipathic compounds suitable for use in the present invention must be able to function as emulsifiers and they must include a biospecific moiety at the head end of their hydrophilic part. Examples of suitable biospecific moieties include but are not limited to a sugar moiety, a peptide moiety, a glycopeptide moiety, a lipoteichoic acid, and an emulsan fragment.

Examples of suitable sugar moieties include but are not limited to β-D-galactose, α-D-galactose, α-D-glucose, β-D-glucose, L-rhamnose, α-L-fucose, α-1,6 dextran, α-D-mannose, β-D-mannose, α-sialic acid, α-N-acetylsialic acid, 2-amino-2-deoxy sugars and their corresponding 2-acetamido derivatives, xylose and mixtures thereof. The examples of 2-amino-2-deoxy sugars include but are not limited to 2-amino-2-deoxy-β-D-glucose, 2-amino-2-deoxy-α-D-glucose, 2-amino-2-deoxy-β-D-galactose, 2-amino-2-deoxy-α-D-galactose. Examples of 2-acetamido-2-deoxy derivatives of 2-amino-2-deoxy sugars include but are not limited to 2-acetamido-2-deoxy-β-D-glucose, 2-acetamido-2-deoxy-α-D-glucose, 2-acetamido-2-deoxy-β-D-galactose, 2-acetamido-2-deoxy-α-D-galactose. The preferred sugar moieties are β-D-galactose, α-1,6-dextran, D-glucose and D-mannose due to a wide range of oral and skin microorganisms that express lectins which recognize these sugar moieties.

The most preferred amphipathic compounds incorporating β-D-galactose are aldobionamides, which have a β-galactosidic linkage and an amide group:

$$-\overset{O}{\overset{\|}{C}}-NR^1R^2$$

wherein $R^1$ and $R^2$ each represents independently a saturated or unsaturated hydrocarbon chain containing up to 24 carbon atoms, and the total number of carbon atoms in $R^1$ and $R^2$ is at least 8, preferably at least 16. Preferably, $R^1$ is hydrogen.

An aldobionamide is defined herein as the amide of an aldobionic acid. The aldobionic acid is a sugar substance (e.g., any cyclic sugar) wherein the aldehyde group (generally found at the $C_1$ position of the sugar) has been replaced by a carboxylic acid. Aldobionamides are based on compounds comprising more than one saccharide unit; they may be based on compounds comprising two saccharide units (e.g., lactobionamide or maltobionamide) or they may be based on compounds comprising more than two saccharide units as long as the polysaccharide has a terminal sugar unit with an aldehyde group available for oxidation.

Aldobionamides are most preferred amphipathic compounds to be included in the inventive emulsions due to the dual function they may serve in the emulsions according to the invention: in addition to being biospecific amphipathic agents they also have antimicrobial activity (see Example 11).

An example of a suitable aldobionamide is a compound of Formula A, which is a lactobionamide.

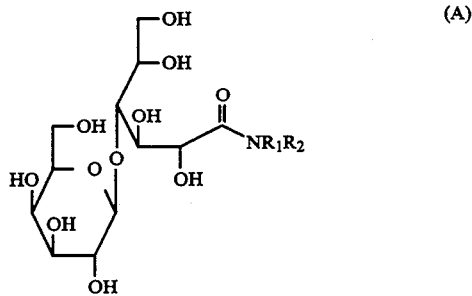

The most preferred compound is a compound of Formula A, wherein $R^1$ is hydrogen and $R^2$ is a $C_{16}$ hydrocarbon chain.

Aldobionamides suitable for use in the present invention and preparation thereof are more fully described in a commonly assigned application Ser. No. 07/981,707, now U.S. Pat. No. 5,310,542, which is incorporated by reference herein.

Examples of amphipathic compounds containing an α-1,6-dextran moiety are polysaccharide hydrolyzates which contain an α-1,6-dextran (i.e., oligosaccharides containing α-1,6-dextran) covalently bonded to an alkylamine; these amphipathic compounds are secondary or tertiary amines, wherein the alkyl chains may be saturated or unsaturated and contain the total of at least 16 carbon atoms. Secondary amines are preferred. Such molecules can be obtained by reductive amination of the oligosaccharide, as described in U.S. Pat. No. 2,016,962 to Flint et al., which patent is incorporated by reference herein.

Amphipathic compounds containing D-glucose as the biospecific moiety may be the α-1,6-dextran containing compounds, discussed above. However, it is not necessary to have a complete α-1,6-dextran moiety in order to have a D-glucose-containing amphipathic compound recognizable by lectins on various microorganisms.

Amphipathic compounds containing D-glucose, suitable for use in the present invention may be obtained in a way analogous to the synthesis of α-1,6-dextran-containing compounds, described above. Additional methods of preparation of D-glucose or D-mannose containing amphipathic compounds are described in U.S. Pat. No. 3,839,318, incorporated by reference herein. The method includes the following steps:

In a 500 ml three necked flask equipped with stirrer, vacuum connection and a thermometer is placed 1.62 moles of N-alkanol and 1.0 gram of concentrated sulfuric acid. 0.50 mole of glucose or mannose is added and the pressure is adjusted to 40 mm Hg. The reaction mixture is heated to 90° C. to 95° C. in 30 min. It is maintained at 95° C. to 100° C. and 40 mm Hg for 45 mins. The mixture is neutralized with sodium hydroxide and distilled. The product is a mixture of alkyl glucoside or alkyl mannoside and alkyl oligosaccharide.

Examples of suitable aphipathic compounds containing D-glucose or D-mannose include, but are not limited to: octyl glucoside, dodecyl glucoside, tetradecyl glucoside, decyl mannoside, dodecyl mannoside.

Examples of suitable peptide moieties include but are not limited to petides having the following amino acid sequences:

ARG-GLY-ASP
ARG-GLY-ASP-SER
ARG-GLY-ASP-SER-PRO-ALA-SER-SER-LYS-PRO
ARG-GLY-GLU-SER
ARG-PHE-ASP-SER
GLY-ARG-GLY-ASP

ARG-GLY-ASP peptide moiety is preferred because it is recognized by intergrins and bacteria. The preparation of amphipathic compounds containing peptide moieties is described in "Enzymafic Synthesis of Surfactants" by Evgeny N. Vulfson in Surfactants in Lipid Chemistry, J. H. P. Thyman, p. 16, Royal Society of Chem., Thomas Graham House, Cambridge. In general, amphipathic compounds incorporating peptide moieties are amino acid esters or amino acid amides. Typically, amino acid esters are prepared by reacting amino acids or their derivatives with fatty acid chlorides or anhydrides. The synthesis of amino acid esters is described in greater detail in M. R. Infante et al., J. Am. Oil Chem. Soc., 1989, 66, 1835, incorporated by reference herein and S. Y. Mhaskar et al. J. Am. Oil Chem. Soc., 1990, 67, 1015, incorporated by reference herein. The synthesis of amino acid amides is typically an enzymatic synthesis as described by Montet et al., J. Am. Oil Chem. Soc., 1990, 67, 771, incorporated by reference herein. Montet et al. have prepared ε-N-acyl-L-lysines using the amino acid and vegetable oils as substrates. The products were obtained in 35%, 60% and 73% yield after 1, 4 and 7 days incubation at 90° C. respectively. The reaction was also shown to proceed under solvent-free conditions.

Suitable amphipathic compounds incorporating a biospecific glycopeptide moiety include but are not limited to η-casein, desialylated derivatives of κ-casein, fetuin, desialylated derivatives of fetuin, and mixtures thereof.

κ-casein is a natural surfactant glycoprotein found in milk. It can be used as a biospecific amphipathic compound, without modification, to take advantage of its oligosaccharidic terminal sialic acid group or it can be treated (after Neeser, J., et al., Infection and Immunity, Vol 56, 12, p. 3201-3208, December 1988) to remove the terminal sialic acid groups with subsequent exposure of penultimate β-galactose moieties. κ-casein and its desialylated derivatives are more fully described in U.S. Pat. No. 4,992,420 and U.S. Pat. No. 4,994,441, both of which are incorporated by reference herein.

Fetuin is a natural glycoprotein found in bovine fetal fluid. It can be used as a biospecific compound, to take advantage of its terminal sialic acid groups and penultimate β-galactose groups. Fetuin and desialylated fetuin may be obtained from Sigma.

A lipoteichoic acid is a major component of walls of a number of bacteria, accounting for 20 to 60% of the dry weight of cell walls. Lipoteichoic acid compounds are amphipathic. A general formula for a lipoteichoic acid is as follows:

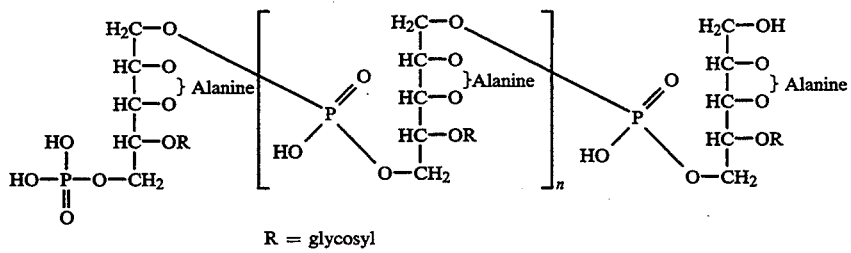

R = glycosyl

In lipoteichoic acid compounds suitable for use in the present invention R contains at least 8 carbon atoms, and may contain up to 24 carbon atoms. Lipoteichoic acid is obtained from bacterial sources. Lipoteichoic acid is available commercially from Sigma.

Emulsan is a natural biopolymer produced by *Acinetobacter calcoaceticus* to emulsify oils for its metabolic degradation. The polymer has an approximate molecular weight of one million and consists of a carbohydrate backbone of N-acetylgalactosamine, glucose and an aminouronic acid. Pendant from the carbohydrate backbone are N- and O-linked fatty acids from eight to eighteen carbons in length. Some of these fatty acid moieties are α- and β-hydroxy acids. In its native state, the polymer is produced by the bacterium in conjunction with a protein which aids in heavy oil emulsification. This protein is removed in processing for commercial use.

Emulsan can be obtained according to the method described in U.S. Pat. No. 4,81 8,817, incorporated by reference herein. According to the present invention, emulsan is hydrolyzed. The resulting emulsan hydrolyzate is an amphipathic compound which can be employed as such, without further modification.

According to the present invention, amphipathic compound constitutes from about 0.05% to about 10% by weight of the emulsion, preferably 0.1% to 10% in order to maximize the stability of the emulsion. The amphipathic compound may be part of an emulsifier system used in compositions according to the invention. If used, such other emulsifiers may be used to make the total level of emulsifier system in compositions according to the invention to be between 0.05–10% by weight, more preferably 0.1–10% by weight.

Oil Phase

The inventive emulsions contain oil droplets which serve as a substrate for an amphipathic compound. According to the present invention, it is by virtue of the association of an oil droplet with an amphipathic compound that a multiple binding site for a microorganism or a biological surface is provided.

Suitable oils are selected from the group consisting of mineral oils, hydrocarbons, silicone oils, triglyceride/-ester oils, essential oils, and mixtures thereof.

When the inventive emulsion is intended for application in an oral cavity, a pharmaceutically acceptable oil must be used.

When the inventive emulsion is intended for topical application to mammalian skin, hair, or nails, examples of suitable oils include but are not limited to: silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil.

The preferred oils are common oils such as corn oil, paraffin oil or neat and mixed essential oils, due to their ready availability.

According to the preferred embodiment of the invention the oil phase of the inventive emulsions further includes a lipophilic ingredient which is delivered to the surface of a microorganism and/or to a biological surface.

A lipophilic compound, as defined herein, is a compound which dissolves in fatlike solvents. While the compounds suitable for use herein may have minimal solubility in water, their solubility in fatlike solvents is substantially greater. Generally, the solubility of a lipophilic compound in a fatlike solvent should be high enough to prepare at least 1% solution of the compound in the fatlike solvent. Further, the lipophilic compound should be soluble in the chosen oil. Preferably, the minimal solubility of the lipophilic compound in the oil is at least 0.01 g of the compound per 1 g of the oil.

When the desired target surface is an oral microorganism, or teeth, or an oral epithelial surface the lipophilic material is generally selected from the group consisting of an antimicrobial compound, a flavorant, and mixtures thereof. Suitable flavorants include but are not limited to wintergreen oil, oregano oil, bay leaf oil, peppermint oil, clove oil, sage oil, sassafras oil, lemon oil, orange oil, anise oil, benzaladehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof. Suitable antimicrobial compounds include but are not limited to thymol, menthol, triclosan, 4-hexylresorcinol, phenol, eucalyptol, benzoic acid, benzoyl peroxide, butyl paraben, salicylamides, and mixtures thereof.

When the desired target surface is mammalian skin, hair, or nails, suitable lipophilic materials include but are not limited to skin anti-ageing compounds, skin conditioning compounds, vitamins, perfumes, antimicrobials, UV-absorbing materials, anti-acne agents, anti-cellulite compounds and mixtures thereof.

Suitable anti-ageing and conditioning compounds include but are not limited to retinoids, fat-soluble vitamins, ascorbyl palmitate, ceramides, pseudoceramides (e.g., pseudoceramides described in U.S. Pat. Nos. 5,198,210; 4,778,823; 4,985,547; 5,175,321, all of which are incorporated by reference herein), phospholipids (e.g., distearoyl lecithin phospholipid), fatty acids, fatty alcohols, cholesterol, plant sterols, and mixtures thereof. Preferred fatty acids or alcohols are those that have straight or branched alkyl chains containing 12–20 carbon atoms. A particularly preferred fatty acid is linoleic acid since linoleic acid assists in the absorption of ultraviolet light and furthermore is a vital component of the natural skin lipids. The term "retinoid" as used herein includes all natural and/or synthetic analogues of vitamin A or retinal like compounds which possess the biological activity of vitamin A in the skin as well as the geometric isomers and stereoisomers of these compounds such as all-trans and 13-6 retinoid acid.

Suitable vitamins include but are not limited to vitamin A and vitamin A derivatives, vitamin $B_2$, pantothenic acid, vitamin D, vitamin E.

Suitable UV-absorbing materials include but are not limited to PABA and PARA amino benzoate derivatives, salicylates, cinnamates, anthranilates, dibenzoyl methanes, camphor derivatives and mixtures thereof. Specific examples include but are not limited to: benzophenone-3, benzophenone-8, ethyldihydroxypropyl-PABA, glyceryl PABA, octyldumethyl PABA, Parsol 1789® (i.e., butyl methoxy debenzoyl methane), homosalate, menthyl anthranilate, octocrylene, octylmethoxy cinnamate, TEA salicylate, octyl salicylate, and mixtures thereof.

Suitable anti-cellulite agents include but are not limited to isobutylmethylxanthine, caffeine, theophylline, yohimbine, and mixtures thereof.

Suitable lipophilic anti-acne agents include but are not limited to resorcinol, resorcinol acetate, benzoyl peroxide, salicylic acid, azaleic acid, long chain dicarboxylic acids, and mixtures thereof.

Of course other lipohilic ingredients, not listed in the specific lists or categories above, are suitable for inclusion in the inventive emulsions, as long as they are soluble in an oil phase.

The amount of the lipophilic compound in the present compositions typically ranges from 0.01 to 10% by weight, preferably from 0.05 to 5%, most preferably from 0.1 to 3%. Generally, no upper limit on the concentration of the lipophilic compound exists. Increased concentration of the lipophilic compound in the oil phase may lead to an increased delivery of the lipophilic compound to the surface of a microorganism or to a biological surface.

When the lipophilic compound is a phenolic antimicrobial (e.g., thymol or triclosan), preferably at least 0.05%, most preferably 0.1 to 3%, is included in the compositions in order to provide an antimicrobial benefit at an optimum cost. Salicylamides are typically employed in the amount of at least 0.01%, preferably from 0.05 to 3%, most preferably from 0.1 to 2%. When the lipophilic compound is a flavoring agent, the amount typically ranges from 0.01 to 5%, preferably from 0.1 to 3%.

It should be noted that some lipophilic active may perform more than one function. For instance, menthol may perform both an antimicrobial and flavoring function; fat-soluble vitamins are nutrients for skin, and also serve as conditioning and anti-wrinkle actives.

The oil phase constitutes from 1% to 70%, preferably from 5% to 50%, most preferably from 10% to 30% by weight of the emulsion.

Aqueous Phase

The aqueous phase comprises from about 30% to about 99%, preferably from 50% to 95%, most preferably from 70% to 90% by weight of the inventive emulsions. The aqueous phase may contain water soluble ingredients for inclusion in compositions to be delivered to mammalian oral cavity or to mammalian skin, hair and nails.

The preferred oral compositions of the present invention are in the form of toothpaste creams, or gels, or mouthwashes. Ingredients typically included in toothpastes and gels may be used in toothpaste and gel compositions in accordance with the invention. Suitable ingredients include abrasive polishing materials, sudsing agents, flavoring agents, humectants, binders and sweetening agents.

Abrasives which may be used in the compositions of the invention include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethyl methacrylate, powdered polyethylene, silica xerogels, hydrogels and aerogels and the like. Also suitable as abrasive agents are calcium pyrophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, polyethylene glycols, propylene glycol, hydrogenated partially hydrolyzed polysaccharides and the like. The humectants are generally present in amounts of from 0 to 80%, preferably 5 to 70% by weight, particularly for toothpastes. Thickeners suitable for use in the invention include silica. Thickeners may be present in toothpaste creams and gels at 0.1 to 20% by weight.

Sweeteners suitable for use in the present dentifrice, preferably at levels of about 0.1% to 5%, include saccharin.

Certain pyrophosphate and other polyphosphate salts have been disclosed in U.S. Pat. Nos. 4,515,772 and 4,627,977 as being useful as anti-calculus agents. These include di- and tetra-alkali metal pyrophosphates wherein the alkali metals are preferably selected from the group consisting of sodium and potassium. Polyphosphate salts may be included generally in the amount such that it provides for at least 0.5% polyphosphate anions, the upper level being about 10%, preferably about 7.5%.

Zinc salts are disclosed as anti-calculus and anti-plaque agents in U.S. Pat. No. 4,100,269 and in U.S. Patent Nos. 4,416,867, 4,425,325 and 4,339,432. Preferred compositions of the invention include zinc salts, particularly zinc citrate. The zinc compounds may be present in the compositions in amounts sufficient to furnish about 0.01% to about 4% zinc, or preferably about 0.05% to about 1%, zinc ion.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anti-caries benefit. Preferred compositions of the invention include the fluoride source. Fluoride ions are typically provided at a level of from 0 to 1500 ppm, preferably 50 to 1500 ppm, although higher levels up to about 3000 ppm may be used.

Flavors are usually included in toothpastes in low amounts, such as from 0.01 to about 5% by weight, especially from 0.1% to 5%.

Water-soluble antibacterial agents, such as chlorhexidine digluconate, hexetidine, alexidine, quaternary ammonium anti-bacterial compounds and water-soluble sources of certain metal ions such as zinc, copper, silver and stannous (e.g., zinc, copper and stannous chloride, and silver nitrate) may also be included.

Titanium dioxide is a suitable whitener.

Dyes/colorants suitable for dentifrices, i.e., FD&C Blue #1, FD&C Yellow #10, FD&C Red #40, etc., may be employed in the dentifrices of the invention.

Various other optional ingredients may be included in the compositions of the invention. Examples include, but are not limited to, preservatives, vitamins such as vitamin C and E, other anti-plaque agents such as stannous salts, copper salts, strontium salts and magnesium salts. Also included may be pH adjusting agents, anticaries agents such as urea, calcium glycerophosphate, sodium trimetaphosphate, silicone polymers, plant extracts, desensitizing agents for sensitive teeth such as potassium nitrate and potassium citrate, and mixtures thereof.

Ingredients mentioned above as suitable for toothpastes are generally suitable for gels, as will be apparent to one of skill in the art of toothpaste and gel formulation. Thus, except where otherwise noted, references to toothpastes are to be construed as applying to gels as well.

Typically, mouthwashes comprise a water/alcohol solution, flavor, humectant, sweetener, sudsing agent, and colorant. The corresponding compounds mentioned above which are used in toothpastes, are generally suitable within the ranges above for mouthwashes as well. The mouthwash can include ethanol at a level of from 0 to 60%, preferably from 5 to 30% by weight, however, alcohol should not be present in the amounts that would affect the stability of the emulsion.

The inventive emulsions are incorporated into dentifrice or mouthwash compositions in the same manner as any other ingredient is incorporated in such compositions. For instance, in toothpaste preparation the emulsion is added with stirring to the main toothpaste mix.

The compositions suitable for topical application to human skin, hair, or nails may be in the form of a lotion, a cream, a spray, a shampoo, a mousse, and the like.

Examples of conventional adjuncts which can optionally be employed in the inventive compositions for application to mammalian skin, hair or nails include preservatives, such as parahydroxy benzoate esters; antioxidants, such as butyl hydroxy toluene; humectants, such as glycerol, sorbitol, 2-pyrrolidone-5-carboxylate, dibutylphthalate, gelatin, polyethylene, glycol, preferably PEG 200-600; buffers, such as lactic acid together with a base such as triethanolamine or sodium hydroxide; waxes, such as beeswax, ozokerite wax, paraffin wax; plant extracts, such as Aloe vera, cornflower, witch hazel, elderflower, cucumber; thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

The topical composition according to the invention is intended primarily as a product for topical application to human skin. The composition can also be applied to hair and nails.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The following specific examples further illustrate the invention but the invention is not limited thereto.

EXAMPLE 1

Preparation of Amphipathic Compounds

Synthesis for N-hexadecyl lactobionamide

In a 5 L three necked round bottom flask equipped with a condenser and mechanical stirrer, lactobiono-1,5-lactone (400 g) was dissolved in warm methanol (3.5 L, 50°–55° C.). Melted hexadecylamine (1.0 eq., 284 g) was then added. The reaction was cooled to room temperature followed by stirring overnight to allow complete crystallization. The desired white product was filtered and recrystallized from methanol in 91% isolated yield. The methanol filtrate contained a mixture of N-hexadecyllactobionamide and hexadecylammonium lactobionate.

$\eta$-casein and Desialylated derivative of $\eta$-casein

Fifty milligrams of $\kappa$-casein (Sigma) were dissolved in 5ml of 25 mM $H_2SO_4$ and the solution was held at 80° C. for two hours. The solution was then cooled to room temperature and neutralized with NaOH. This procedure removes sialic acid moieties while leaving the remainder of the oligosaccharide side-chain intact (after Neeser et al., Infection and Immunity, December 1988 pp. 3201–3208). As a control, 50 mg of $\eta$-casein were placed in 5ml of distilled water, held at 80° C. for two hours and cooled to room temperature. An appropriate amount of $Na_2SO_4$ (0.0176 g) was added so that both solutions were equivalent in sodium and sulfate concentration. Test emulsions were then formed using one part oil and four parts $\kappa$-casein solution.

Synthesis for N-hexadecyl Gluconamide

In a 5 L three necked round bottom flask equipped with a condenser and mechanical stirrer, Glucono-1,5-lactone (178 g) was dissolved in warm methanol (3.5 L, 50°–55° C.). Melted hexadecylamine (1.0 eq., 241 g) was then added. The reaction was cooled to room temperature followed by stirring overnight to allow complete crystallization. The desired white product was filtered and recrystallized from methanol in >95% isolated yield.

Preparation of N-hexadecyl maltobionamide

Maltobiono-1,5-lactone (10 g, 1 eq) was dissolved in methanol (40 ml, 50° C.). Hexadecylamine (6.45 g, 0.93 eq) was added slowly. The reaction was cooled to room temperature. The product was filtered. Recrystallization from methanol gave 85% yield of N-hexadecyl maltobionamide.

EXAMPLE 2

Preparation of Emulsions

An amphipathic agent was added to 1.0 mM phosphate buffer (pH 6.8) containing 1.0 mM calcium chloride, 0.1 mM magnesium chloride and 50 mM potasium chloride at 75° C. This solution was mixed with the oil in a 1:4 ratio to be emulsified and sonicated (at 60 watts for 30 seconds) for emulsification with an ultrasonic probe. The concentration of the amphipatheic agent in the resulting oil-in-water emulsion was 1.25%.

The ultrasonic probe employed was Model 185D from the Heat Systems-Ultrasonics, Inc.

EXAMPLE 3

Bacterial Agglutination Assay

A bacterial agglutination assay was used to determine the ability of biospecific emulsions to bind to bacterial surfaces with specificity. *Actinomyces naeslundii* PK29 (abbreviated "AnPk29"), which carries lectins recognizing β-galactose, and *Streptococcus gordonii* G9B (abbreviated "SgG9B"), which caries lectins recognizing sialic acid, were cultured at 37° C. in a medium containing 2.5% tryprone, 1.5% yeast extract, 0.1% magnesium sulfate and 1% fructose (this medium hereinafter abbreviated "TYF"). Cells were then centrifuged and washed two times with 1.0 mM phosphate buffer (pH 6.8) containing 1 mM calcium chloride, 0.1 mM magnesium chloride and 50 mM potassium chloride and resuspended in the phosphate buffer to an absorbance (540 nm) of 1.5.

In a total volume of 2.0 ml phosphate buffer, microorganism, and the tested emulsion, 0.05% Tween 20 and in the appropriate cases, inhibiting sugars and controls were placed in 4.0 ml disposable polystyrene cuvets with plastic covers. The cuvets were rotated at 20 rpm and the absorbance was monitored at 540 nm. Loss of absorbance indicated flocculant interaction between emulsion droplets and bacteria. Biospecific emulsion was prepared as described in Example 2, with hexadecyllactobionamide as an amphipathic agent; the oil phase contained 10% Thymol (from Givaudan Co.)in a corn oil (Mazolae ®).

The results that were obtained are summarized in Table 1:

TABLE 1

| SAMPLE | CUVETTE CONTENT | % OF INITIAL ABSORBANCE |
| --- | --- | --- |
| 1 | An Pk29 + Emulsion | 75 |
| 2 | AnPk29 + Emulsion + Lactose (80 mg/ml) | 99 |
| 3 | An Pk29 + Emulsion | 74 |
| 4 | An Pk29 + Emulsion + Melibiose (80 mg/ml) | 71 |

This assay showed that AnPk29 recognized emulsion droplets containing hexadecyl lactobionamide and that flocculation was caused by this interaction (Samples 1 and 3). This interaction was inhibited by lactose (Sample 2) and was not affected by melibiose (Sample 4), a disaccharide which does not contain β-galactose demonstrating that the droplet/microbe interaction was mediated by the biospecific carbohydrate head group of the amphipathic agent.

EXAMPLE 3A

A bacterial agglutination assay as described in Example 3 was employed, except that in some samples, alkylpolyglycoside (APG 325 from Henkel) was used as an emulsifier in place of a biospecific amphipathic agent. Only Sample 1 contained Thymol.

The results that were obtained are summarized in Table 2.

TABLE 2

| SAMPLE | CUVETTE CONTENT | % OF INITIAL ABSORBANCE |
| --- | --- | --- |
| 1 | Sg G9B + Hexadecyl lactobionamide Emulsion | 99 |
| 2 | An Pk29 + APG Emulsion | 100 |
| 3 | Sg G9B + APG Emulsion | 100 |

*Streptococcus gordonii* G9B, which does not recognize β-galactose, did not interact with the hexadecyl lactobionamide emulsion droplets (Sample 1). Emulsions formed with alkyl polyglycosides did not interact with either microbe (Samples 2 and 3). All results were confirmed with optical microscopy (Leitz Dialux 22 microscope): no intereaction between microorganisms and oil droplets was observed in any of the samples.

EXAMPLE 4

A bacterial agglutination assay as described in Example 3 was employed, except that κ-casein or a desialylated derivative thereof was used as an emulsifier in place of hexadecyl lactobionamide. None of the samples contained Thymol.

The results that were obtained are summarized in Table 3.

TABLE 3

| SAMPLE | CUVETTE CONTENT | % OF INITIAL ABSORBANCE |
| --- | --- | --- |
| 1 | Sg G9B | 100 |
| 2 | Sg G9B + Desialylated κ-casein Emulsion | 100 |
| 3 | Sg G9B + κ-casein emulsion | 22 |
| 4 | An Pk29 | 100 |
| 5 | An Pk29 + Desialylated κ-casein Emulsion | 6 |
| 6 | An Pk29 + κ-casein emulsion | 80 |

*Streptococcus gordonii* G9B were flocculated by emulsions made with intact κ-casein but were not affected by emulsions prepared with desialylated κ-casein (Sample 2). *A. naeslundii* were flocculated by desialylated κ-casein emulsions (Sample 5) but were less affected by intact κ-casein emulsions (Sample 6): intact κ-casein contains some terminal β-galactose groups, although it predominantly contains β-galactose groups in penultimate positions. Accordingly, maximum recognition by AnPK29 is observed in Sample 5, which employed desialylated κ-casein emulsion in which β-galactose groups are exposed.

EXAMPLE 5

Surface-Associated Bacterial Adsorption Assay

This assay was employed to determine the ability of emulsion droplets to adsorb specifically to an adherent layer of microbes. Microbial cultures were prepared as described above. Three ml of a suspension of *Streptococcus gordonii* G9B (absorbance of 1.5) were placed in 10 mm×35 mm polystyrene petri dish and centrifuged at 1000×g for 5 minutes. The supernatant was discarded and the plate was washed extensively with phosphate buffer. One ml of an oil-in-water emulsion (prepared with κ-casein or a desialyated derivative thereof, as described in Example 2) was added to the dish which was placed on an orbital agitator table for one minute. The dishes were then rinsed thoroughly with buffer and evaluated by optical microscopy (Leitz Dialux 22 microscope) by counting the number of droplets adhering per microscope field.

The results that were obtained are summarized in Table 4.

TABLE 4

| | Droplet Deposition on Sg G9B | |
|---|---|---|
| SAMPLE # | EMULSION TYPE | # OF DROPLETS ADHERED |
| 1 | Emulsion with κ-casein | 50 ± 13 |
| 2 | Emulsion with desialylated derivative of κ-casein | 5 ± 3 |

Results showed that on a layer of *S. gordonii* G9B, which recognizes sialic acid, emulsion droplets incorporating intact κ-casein adsorbed to a far greater degree (Sample 1) than droplets containing desialylated κ-casein (Sample 2), indicating that emulsion droplets were specifically targeted and significantly substantive to the layer of *S. gordonii*.

EXAMPLE 6

Amine-Modified Latex Bead Agglutination Assay

Amine-modified latex beads (Polysciences, Inc.) with an average diameter of 3.5 microns were covalently linked to hydrolysis products from α-1,6 dextrans Av.M.W.=10,000 (Pharmacia®, T10). One percent solutions of dextran were held at 60° C. for 40 hours in 0.1M HCl. They were then neutralized with sodium hydroxide and enough dibasic sodium phosphate was added to make a 0.1M phosphate solution of approximately pH 9.0. The latex beads were added to the neutralized dextran solutions (5 milligrams/ml) and the mixture was held at 37° C. for 24 hours with gentle agitation. The solutions were then centrifuged (2500×g, 10 minutes) and washed with the phosphate buffer mentioned above three times and resuspended to the original volume in phosphate buffer.

These amine-modifed latex beads had dextran hydrolysate products covalently linked to their surfaces and were used as the functional equivalent of emulsion droplets formed with biospecific amphipathic compounds.

For Sample 8, beads were treated with bovine serum albumin (from Sigma) via the same procedure as described above.

Four ml polystyrene cuvets with plastic caps containing a final sample volume of 2.0 ml were used in an absorbance assay similar to the bacterial agglutination assay previously mentioned. The test sample contained 0.05% Tween 20, latex beads, phosphate buffer, microbial cells and carbohydrate inhibitor where appropriate. The cuvettes were rotated at 20 rpm and loss of absorbance was monitored spectrophotometrically at 540 nm. The test species were *Streptococcus sobrinus* 6715 (abbreviated "Ss 6715") which is associated with human caries and carries lectins which recognize α-1,6 dextran oligosaccharides and *Staphylococcus epidermidis* (abbreviated "SE") which carries lectins recognizing D-glucose moieties. These microbes were cultivated with the same procedure mentioned above.

The results that were obtained are summarized in Table 5.

TABLE 5

| SAMPLE | CUVETTE CONTENT | % OF INITIAL ABSORBANCE |
|---|---|---|
| 1 | Ss 6715 + untreated beads | 100 |
| 2 | Ss 6715 + α-1,6 dextran treated beads | 67 |
| 3 | Ss 6715 + α-1,6 dextran treated + T10 (1 mg/ml) | 89 |
| 4 | Ss 6715 + α-1,6 dextran treated beads + T10 (2 mg/ml) | 93 |
| 5 | Ss 6715 + α-1,6 dextran treated beads + TN10 (3 mg/ml) | 96 |
| 6 | SE + α-1,6 dextran treated beads | 86 |
| 7 | SE + α-1,6 dextran treated beads + glucose (50 mg/ml) | 93 |
| 8 | SE + Bovine serum albumin treated beads | 99 |

Results show that *S. sobrinus* recognized and adsorbed to α-1,6-treated beads (Sample 2) and that the interaction was effectively inhibited by α-1,6 dextran in a dose dependent manner (Samples 3–5). *S. epidermidis* recognized and adsorbed to the same beads (Sample 6) and this interaction was inhibited by D-glucose (Sample 7). Ss6715 did not interact with untreated beads (Sample 1). *S. epidermis* did not interact with bovine serum albumin treated beads (Sample 8)-bovine serum albumin does not contain glucose moieties.

EXAMPLE 7

Bacterial Monolayer Regrowth Assay

Polystyrene 96-well ELISA plates, the surfaces of which were modified to carry maleic anhydride (Pierce Reacti-Bind Maleic Anhydride Activated Polystyrene Plates), were used to form a living layer of bacteria covalently bound to the surface of the plates. AnPK29 culture was grown as described in Example 3, washed and resuspended in 0.1M phosphate, 0.15M NaCl, pH 7.2 buffer (PBS). Aliquots of bacterial suspension were placed in each well, centrifuged (500 ×g, 10 minutes) and each plate was incubated at 37° C. for one hour. Following rinsing with sterile buffer, the wells were treated for one minute with test emulsions, also sterile buffer. All supernatant liquids were removed by aspiration with a Pasteur piper. After two rinses with sterile buffer, TYF medium was added to each well and the plate was incubated at 37° C. for an appropriate time, usually eight to twenty hours. A spectrophotometric plate reader (Dynatech MR7000®) was used to monitor the turbidity (extent of regrowth) in the wells. A higher reading indicates regrowth.

The results that were obtained are summarized in Table 6.

TABLE 6

| Bacterial Monolayer Regrowth | | |
|---|---|---|
| $C_{16}$-Lactobionamide Emulsion vs. $C_{16}$-Gluconamide Emulsion | | |
| SAMPLE # | TREATMENT | Absorbance ± S.D. |
| 1 | Buffer only | 1.45 ± |
| 2 | $C_{16}$ Lactobionamide Emulsion | .20 ± .01 |
| 3 | $C_{16}$ Gluconoamide Emulsion | 1.47 ± .01 |

Results indicate that *A. naeslundii* PK29 regrowth was completely inhibited by emulsions containing corn oil and hexadecyl lactobionamide but was unaffected by emulsions containing corn oil and hexadecyl gluconamide. *A. naeslundii* carries the lectin which recognizes the β-galactose structure contained in the hydrophilic head group of the hexadecyl lactobionamide.

EXAMPLE 8

Example 7 was repeated with N-hexadecyl lactobionamide emulsion. Emulsions of different dilutions, with or without thymol were employed. When thymol was included, thymol was present in the amount of 10% by weight of oil. The results that were obtained are summarized in Table 7.

TABLE 7

Bacterial Regrowth: An PK29
$C_{16}$-Lactobionamide Emulsion with and without Thymol

| SAMPLE | TREATMENT | Absorbance ± S.D. |
|---|---|---|
| 1 | Buffer only | 1.22 ± .02 |
| 2 | Full strength emulsion without thymol | .17 ± .02 |
| 3 | Full strength emulsion with thymol | .18 ± .02 |
| 4 | ¼ strength emulsion without thymol | .17 ± .02 |
| 5 | ¼ strength emulsion with thymol | .17 ± .02 |
| 6 | ⅛ strength emulsion without thymol | .63 ± .05 |
| 7 | ⅛ strength emulsion with thymol | .16 ± .02 |
| 8 | 1/16 strength emulsion without thymol | .77 ± .07 |
| 9 | 1/16 strength emulsion with thymol | .62 ± .03 |

Example 8 demonstrates the effect of the presence of the lipophilic active in the oil phase of biospecific emulsion. No significant differences were observed between samples 2–5: these samples contained a relatively high amount of N-hexadecyl lactobionamide, which is in itself a potent antimicrobial. However, at more dilute concentrations of N-hexadecyl lactobionamide, the inclusion of thymol in the oil phase of biospecific emulsion resulted in a substantially greater antimicrobial effect (Sample 7 vs. Sample 6, and Sample 9 vs. Sample 8).

EXAMPLE 9

Example 7 was repeated, except that SgG9B was employed in place of AnPK29 and κ-casein biospecific emulsion was employed in place of N-hexadecyl aldobionamide emulsions. When thymol was employed, it was present in the amount of 10% by weight of the oil. The results that were obtained are summarized in Table 8.

TABLE 8

Bacterial Regrowth: Sg G9B
κ-casein Emulsion with and without Thymol

| SAMPLE | TREATMENT | Absorbance ± S.D. |
|---|---|---|
| 1 | Buffer only | .54 ± .07 |
| 2 | Full strength emulsion without thymol | .59 ± .06 |
| 3 | Full strength emulsion with thymol | .43 ± .08 |
| 4 | ¼ strength emulsion without thymol | .56 ± .07 |
| 5 | ¼ strength emulsion with thymol | .32 ± .01 |
| 6 | ⅛ strength emulsion without thymol | .58 ± .07 |
| 7 | ⅛ strength emulsion with thymol | .39 ± .03 |

Example 9 demonstrates the criticality of including a lipophilic agent in the oil phase of biospecific emulsions. All samples containing thymol exhibited a significantly greater antimicrobial effect compared to the samples which did not include thymol.

EXAMPLE 10

Hydrolysates of emulsan were prepared as follows:

Two grams of emulsan were placed in 25 ml of 0.5N HCl in a polypropylene centrifuge tube which was placed at 37° C. overnight on a hematology mixer for tumbling. The emulsan suspension was then adjusted to pH 7.0 with NaOH. A 10 ml aliquot was then removed and dialyzed against 100 ml of distilled water through a 1000 MWCO (molecular weight cut off) membrane (from Spectrum Co.) for 24 hrs. Four grams of the dialysate were mixed with one gram of paraffin oil and sonicated for 30 seconds at 150 wafts to form an emulsion. Alternatively, the neutralized hydrolysate was filtered through a 0.2 micron filter and used to form an emulsion as above; this material was of higher molecular weight.

If the emulsion which has been formed from the hydrolysate passed through the 1000 MWCO is placed in a suspension of either *Actinomyces naeslundii* PK29 or *Streptococcus gordonii* G9B, immediate and dramatic agglutination takes place. Both of these organisms are known to recognize N-acetylgalactosamine (2-acetamido-2-deoxygalactose). Microscopic examination showed strong microbe/emulsion droplet interaction. The addition of N-acetyl galactosamine (25 mg/ml) visibly reduced the microbe/emulsion droplet interaction and subsequent agglutination. When the emulsion which had been formed from the hydrolysate passed through the 0.2 micron filter was placed in a suspension of the two organisms, no agglutination occurred. The presence of higher molecular weight material that is not incorporated in emulsion droplets can act to inhibit recognition of similar material of low molecular weight which is incorporated in the oil droplets to prevent agglutination. The difference is believed to be that larger MW material is mostly not incorporated in an oil droplet.

EXAMPLE 11

Various aldobionamides were tested for their bacteriostatic (antimicrobial) effects on the growth of several species of oral bacteria. As shown in Table 9, many N-alkyl lactobionamides displayed considerable antibacterial activity. In several instances, the antibacterial activity of these compounds approached that observed for the anionic surfactant, sodium dodecyl sulfate. Therefore, many of these molecules can deliver multiple benefits when included in the inventive oil-in-water emulsions, i.e., targeting the actively amphilic ingredient and antimicrobial action.

| Tested Compound | *Streptococcus Sanguis* | *Streptococcus sabrinus* | *Actinomyces naeslundii* | *Porphyromonas gingivalis* | *Prevotella intermedius* | *Veillonella dispar* | *Neisseria Subflava* | *Candida albicans* |
|---|---|---|---|---|---|---|---|---|
| Lactobionic Acid | >0.5 | >0.5 | >0.5 | — | — | — | — | — |
| Decylgluconamide | >0.5 | >0.5 | >0.5 | — | — | — | — | — |
| Sodium dodecyl sulfate | 0.0015 | 0.006 | 0.0008 | 0.0008 | 0.0016 | 0.006 | 0.0008 | 0.006 |
| Propyl lactobionamide | >0.1 | >0.5 | >0.5 | >0.1 | >0.1 | >0.1 | >0.1 | >0.1 |

-continued

| Tested Compound | Strepto- coccus Sanguis | Strepto- coccus sabrinus | Actin- omyces naeslundii | Porphyro- monas gingivalis | Prevotella intermedius | Veillonella dispar | Neisseria Subflava | Candida albicans |
|---|---|---|---|---|---|---|---|---|
| Pentyl lactobionamide | >0.1 | >0.5 | >0.5 | >0.1 | >0.1 | >0.1 | >0.1 | >0.1 |
| Octyl lactobionamide | >0.1 | >0.5 | >0.5 | >0.1 | >0.1 | >0.1 | >0.1 | >0.1 |
| Decyl lactobionamide | >0.5 | >0.05 | >0.05 | — | >0.05 | 0.05 | 0.05 | 0.05 |
| Dodecyl lactobionamide | 0.0125 | 0.0125 | 0.006 | 0.003 | 0.025 | 0.006 | 0.025 | 0.0125 |
| Tetradecyl lactobionamide | 0.003 | 0.0125 | 0.0015 | — | 0.0008 | <0.0008 | 0.006 | 0.003 |
| Hexodecyl lactobionamide | 0.0125 | 0.1 | 0.006 | >0.05 | >0.05 | >0.05 | 0.1 | 0.1 |
| Dodecyl-$\beta$-alanyl lactobionamide | 0.0125 | 0.1 | 0.0125 | — | — | — | 0.05 | 0.05 |
| Tetradecyl-glycyl lactobionamide | 0.003 | 0.05 | 0.0008 | — | — | — | 0.05 | 0.05 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. An oil-in-water emulsion suitable for application to the surface of a microorganism or to a biological surface, the emulsion comprising an aqueous phase, an oil phase, and an emulsifier system which comprises an amphipathic compound, wherein the amphipathic compound includes a biospecific moiety at the head end of its hydrophilic group, and wherein the molecular weight of the amphipathic compound is not greater than about